United States Patent
Hayashi

[11] Patent Number: 6,056,713
[45] Date of Patent: May 2, 2000

[54] MOLDABLE CUSTOM-FITTED ANKLE BRACE

[76] Inventor: Melvin M. Hayashi, 339 S. Moorpark Rd., Thousand Oaks, Calif. 91361

[21] Appl. No.: 08/999,756

[22] Filed: Nov. 24, 1997

Related U.S. Application Data

[63] Continuation-in-part of application No. 08/657,875, May 31, 1996, abandoned.

[51] Int. Cl.[7] ........................................ A61F 5/00
[52] U.S. Cl. .................................. 602/27; 602/5; 602/6; 602/8
[58] Field of Search .................................. 602/27, 62, 5, 602/6, 8; 606/215, 216

[56] References Cited

U.S. PATENT DOCUMENTS

| | | | |
|---|---|---|---|
| 5,454,780 | 10/1995 | Duback et al. | 602/8 |
| 5,503,622 | 4/1996 | Wehr | 602/27 |
| 5,676,641 | 10/1997 | Arensdorf et al. | 602/27 |

*Primary Examiner*—John G. Weiss
*Assistant Examiner*—Kelvin Hart
*Attorney, Agent, or Firm*—David O'Reilly

[57] ABSTRACT

This invention relates to a conformable ankle brace constructed of a heat moldable thermoplastic material that can be formed in place around a patient's injured ankle. The moldable thermoplastic material is shaped in a manner that produces medial and lateral extensions for covering the medial and lateral malleoli of a patient's foot. A concave recess is formed between the medial and lateral extensions to improve strength and reduce cracking of the thermoplastic brace. A non-stretchable strap holds the conformable ankle brace in position against the ankle and leg. A stretchable strap secures the medial and lateral extensions or splints in place over the medial and lateral malleoli. Strategically placed pads of hook-textured material, that mate with loop-type material on the fastening straps hold them in place on the ankle brace. Optionally, the moldable custom-fitted ankle brace can beheld in place with athletic tape.

36 Claims, 2 Drawing Sheets

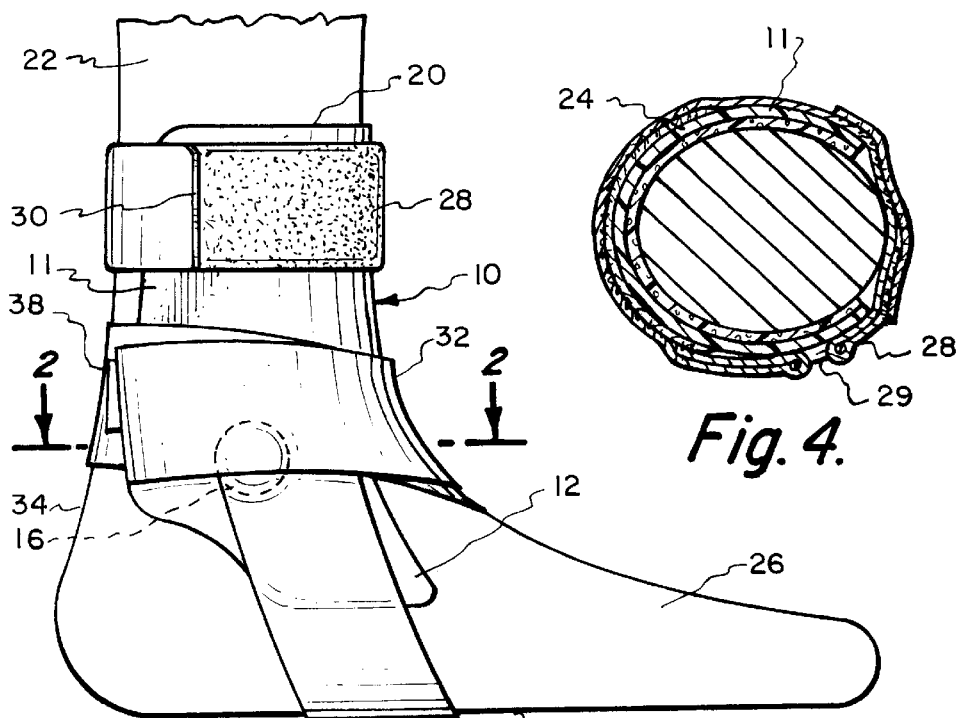
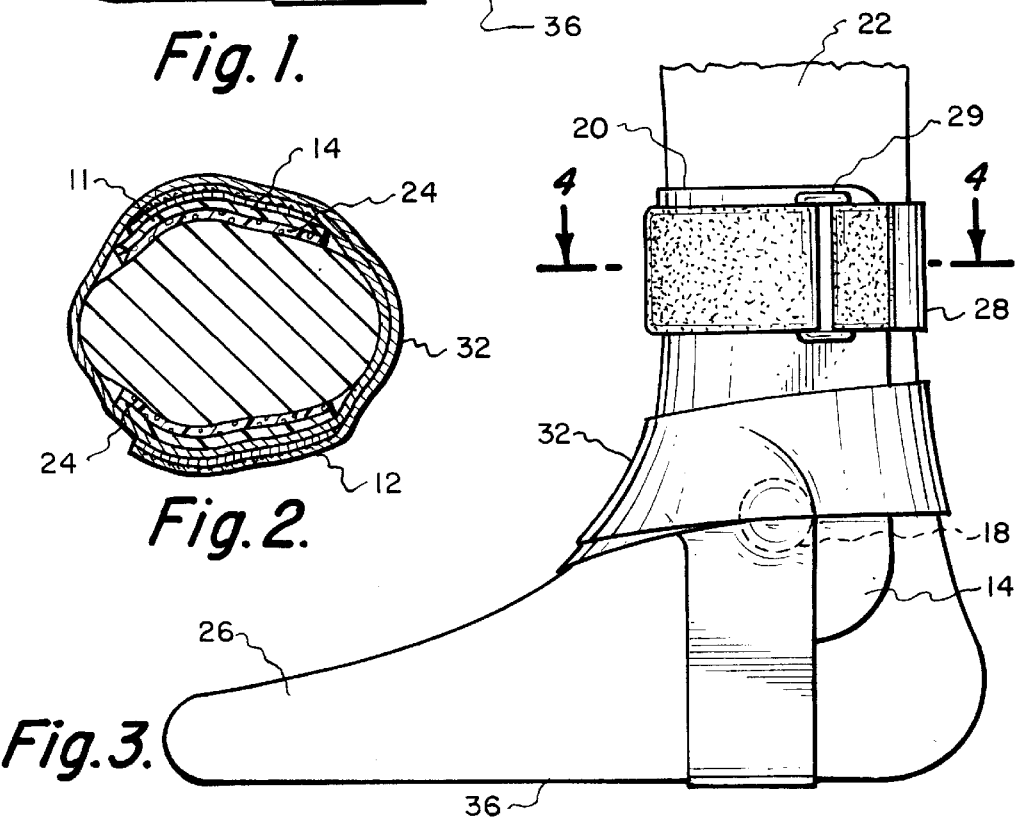

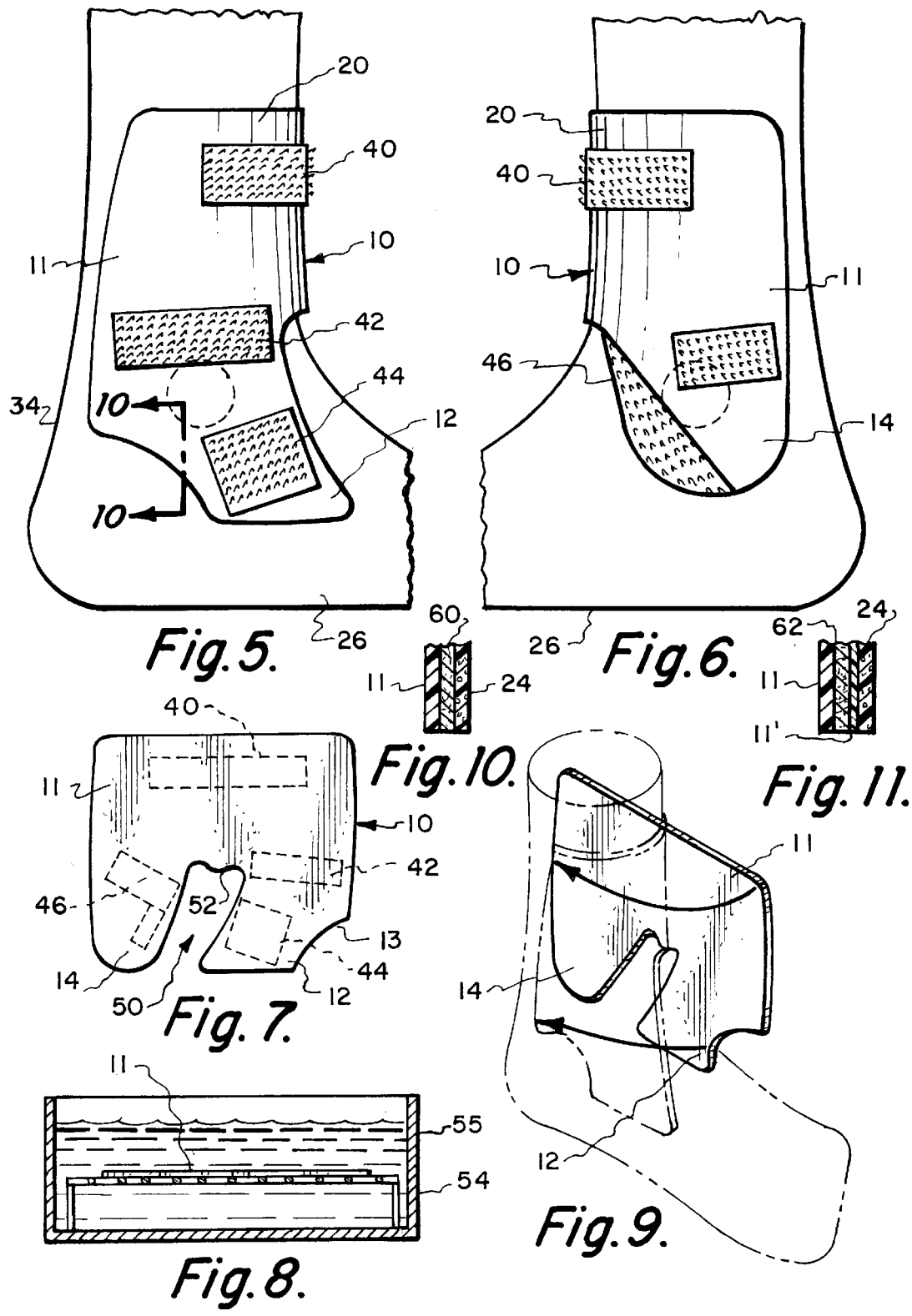

MOLDABLE CUSTOM-FITTED ANKLE BRACE

This application is a Continuation-In-Part application of prior application Ser. No. 08/657,875, filed May 31, 1996, now abandoned.

BACKGROUND OF THE INVENTION

1. Field of the Invention

This invention relates to ankle braces, and more particularly relates to an ankle brace that conforms to the shape of the ankle to provide improved support by decreasing inversion and eversion of the ankle and stabilizing the distal tibia-fibular joint.

2. Background Information

Ankle injuries to workers and athletes are very common and can be debilitating. Most common injuries to the ankle are to the ligaments. The most commonly injured ligaments are the lateral ligaments because injuries most frequently occur when the foot is turned inward. As a result of these injuries, a wide variety of supports and devices have been designed for treating ankle injuries and allow patients to resume use of the ankle.

One such device is in the form of a neoprene resilient sock that is used for acute care of the ankle. This device is effective for treating effusion and edema by providing even compression to the ankle and forefoot region. The support is user friendly and easy to apply. It provides stability and improves stimulus to the ankle and ligaments with its lateral strapping system.

Another device to provide support is produced and manufactured by Bauerfeind & Company, called "Malleoloc." This device is comprised of a pair of splints joined by a stirrup that passes under the arch of the foot. Complicated, color coded VELCRO fasteners (i.e., hook and loop textured material) are provided to apply the support to the foot. The lateral and medial splints are constructed of a preformed thermoplastic to fit behind the medial malleolus bone and in front of the lateral malleolus bone. However, the medial and lateral splints are narrow rigid side supports and provide insufficient support to the ankle. Further, the color coded strap system is complicated to use and it is difficult to achieve a comfortable fit.

Ankle bracing is also used on athletes by completely wrapping the ankle and foot from well above the medial and lateral malleoli, to below the arch of the foot with a strong athletic support tape. This type of ankle bracing requires several layers of tape applied skillfully by a trained technician or doctor. The disadvantages of this type of bracing is that it is costly and time consuming. Tremendous amounts of tape are used for each athletic event. The amount of tape used, and the need for skilled, trained labor makes this method costly.

There are numerous other ankle braces on the market. Each has its own strengths, but all suffer from the same or similar deficiencies. Almost all have separate rigid side supports or splints, and some include a base or stirrup that fits around and under the foot. The side supports extend to approximately the mid-point of the shin, and usually cover the medial and lateral malleoli. These side support walls are generally held in place with straps or belts of some sort. Although the sidewalls are generally padded, they are not comfortable to wear for long periods of time. Few, if any, are practical to wear during strenuous activities such as playing basketball or some other sport. Other braces have difficulty fitting in shoes.

Devices of the type described above are disclosed and described in a number of patents. U.S. Pat. Nos. 4,280,489 and 4,628,945 of Johnson, Jr. describe an ankle brace having outer rigid sheet members that extend from near the bottom of the foot to approximately the mid-point of the shin, over the medial and lateral malleoli. These ankle braces also include a base member that extends around and under the heel, and connects to each side support by hinges.

U.S. Pat. Nos. 4,913,755; 4,844,094 and 5,027,807 of Grim disclose and describe an ankle brace that includes gel filled pads. These gel filled pads provide a resilient support against the ankle and are held in place by rigid side support walls that extend from the mid-point of the shin over the medial malleolus of the ankle. The patents also disclose and describe a stirrup that fits beneath the heel joined to each side support member.

U.S. Pat. Nos. RE33,395 and 5,031,607 to Peters also disclose an ankle brace having rigid side support members hinged to a heel stirrup. The side support members are padded and are held in place with straps.

The disadvantages of each of the devices disclosed in the above is self-evident. The rigid side support members are preformed and while they may have different sizes, do not comfortably support an injured ankle. The rigid stirrup under the foot can be uncomfortable to wear for long periods of time particularly when engaged in some active sport.

It is therefore, one object of the present invention, to provide a single piece conformable ankle brace that conforms to the shape of the wearer's ankle.

Yet another object of the present invention is to provide a conformable ankle brace that is adjustable by heating and reforming the brace.

Still another object of the present invention is to provide an ankle brace that is conformable to the wearer's ankle and includes straps that can be configured to provide the most comfort for the wearer. The brace can also be fitted and held in place with different types of tapings.

Yet another object of the present invention is to provide a conformable ankle brace constructed of a thermoplastic material having a foam liner that is simple and easy to shape to the ankle of each individual. The ankle brace decreases inversion by a medial support. The ankle brace decreases eversion by lateral support of the tibia-fibular in a clamping vise-like action.

BRIEF DESCRIPTION OF THE INVENTION

The purpose of the present invention is to provide a conformable ankle brace that can be formed to fit the shape of an injured ankle to provide maximum support with minimum discomfort to the wearer's injured ankle. The ankle brace of the invention provides better motion in the plantar flexion and dorsiflexion without a hinge.

This invention relates to a conformable ankle brace that wraps around and covers approximately 60 to 80 percent of the leg adjacent the ankle being treated. It is constructed of a thermoplastic material that is soft and pliable when heated, provides a rigid strong support at normal ambient temperatures. The conformable ankle brace is also adaptable to various size ankles and could include an integral shin guard. Removable fastening straps, held in place by hook and loop textured material, allow positioning and adjustments that are most comfortable to the patient permitting the patient to often resume normal activities. The ankle brace can also be fitted and held in place with athletic tape. The conforming custom-fit permits athletes to engage in selected sports activities almost without interference and with minimum discomfort.

The present invention is comprised of a flat sheet of thermoplastic material cut in a pattern that allows it to be easily formed to the shape of a wearer's ankle. The material is preferably lined with a resilient foam material to provide some padding and comfort to the wearer.

The conformable ankle brace is comprised of a thermoplastic sheet cut in a pattern having a substantially rectangular portion and extensions separated by a channel. The extensions provide splints that fit over the medial malleolus and the lateral malleolus when the thermoplastic material is heated and formed around an injured ankle. The inner end or terminus of the channel has a convex shape so that when the brace is form-fitted to the shape of the wearer's ankle, it substantially decreases a tendency of the thermoplastic material to crack and provides additional material to strengthen the brace.

To price a wide range of applications, several sizes will be provided for accommodating different size ankles. A unique advantage of the brace is that when heated, the thermoplastic material may be easily formed and also, may be trimmed to comfortably fit the shape and configuration of the wearer's ankle. The thermoplastic material used is formed around a wearer's ankle, and can be easily marked by simply scribing the material with any semi-sharp instrument or even simply a fingernail. The ankle brace can then be easily trimmed with scissors for the most comfortable fit with maximum support to the injured ankle. The brace increases the stabilization of the distal tibia-fibular joint by a clam shell clamping vise-like action.

This conformable brace is constructed with pads comprised of hook textured (i.e., VELCRO) material that allows the attachment of a loop textured material strap. A hook textural material pad on the shin section, and a longer extension that fits over the medial malleolus and a shorter extension that fits over the lateral malleolus, allow the wearer to configure and attach loop textured material straps at the positions desired. Another unique advantage of the invention is that the conformable ankle brace can be configured to an ankle swollen by injury and later adjusted as the swelling reduces. Thus, the conformable ankle brace can be removed, reheated and reformed to the ankle as the injury heals. The loop textured material straps can be tightened or loosened as needed between hook textured material pads for better support and comfort.

The conformable ankle brace differs from other braces by having a longer, more distal medial extension that preferably extends at least halfway from the medial malleolus to the sole of the foot. The longer medial extension helps decrease pronation and subtalar inversion. No other brace has the length or slope of the distal medial extension to decrease this motion. The molded thermoplastic conforms around the malleoli for better fit and stabilization of the ankle with the loop textured material straps.

The shin portion of the conformable ankle brace can be made in any convenient length and extend all the way to the top of the tibia if desired. A hook textured material pad on the shin portion allows attachment of a heavy duty non-stretchable strap that wraps around the leg and is easily fastened with a D-ring and loop textured material strap, or with adhesive, elastic or athletic tape. Similar hook textured material pads in an intermediate portion about the medial and lateral extension, as well as hook material pads on the extensions themselves, allow the use of a stretchable loop textured material strap for holding the lower extensions in place on the foot and ankle in a figure-eight fashion. The stretchable loop textured strap provides comfortable support beneath the foot, allowing the user to wear it comfortably for longer periods end during strenuous activity such as sports.

An alternative is to wrap the conformable custom-fitted brace with strong athletic tape after fitting the brace. Greater support with much less tape is provided than with conventional athletic taping.

The above and other novel features of the invention will be more fully understood from the following detailed description and the accompanying drawings, in which:

BRIEF DESCRIPTION OF THE DRAWINGS

FIG. 1 is a side elevation of the inner or medial side of a foot with the conformable ankle brace and straps.

FIG. 2 is a sectional view taken at 2—2 of FIG. 1.

FIG. 3 is a side elevation of the lateral or outside of a foot with the conformable ankle brace and straps installed.

FIG. 4 is a sectional view taken at 4—4 of FIG. 3.

FIG. 5 illustrates the conformable ankle brace with hook material pads positioned for fastening attaching straps.

FIG. 6 is an opposite side view of the conformable ankle brace showing the hook material pads for attaching straps.

FIG. 7 is a plan view of the conformable ankle brace before being form fitted to a wearer's foot.

FIG. 8 illustrates the method of heating the conformable ankle brace before applying it to a wearer's ankle.

FIG. 9 illustrates the fitting of the conformable ankle brace to a wearer's foot.

FIG. 10 is a partial sectional view taken at 10—10 of FIG. 5 of an optional alternate construction.

FIG. 11 is a partial sectional view similar to FIG. 10 showing another alternate construction.

DETAILED DESCRIPTION OF THE INVENTION

A conformable ankle brace, constructed and applied to an injured ankle is illustrated in FIG. 1 through 4. Conformable ankle brace 10 is constructed of a thermoplastic material which will be described in greater detail hereinafter, with medial extension 12 and lateral extension 14 designed to cover, stabilize and protect the ankle at the medial and lateral malleoli indicated at 16 and 18 respectively. Upper portion 20, of thermoplastic sheet 11, is designed to strap around and cover a substantial portion (i.e., 70 to 80 percent) of the distal tibia of leg 22. Upper portion 20 of thermoplastic sheet 11 can be formed to extend from just above the ankle to cover the entire tibia if desired.

Thermoplastic sheet 11 may be constructed of any easily formed thermoplastic material, preferably a sheet of NCM Clinic D or similar material approximately ⅛th of an inch thick allowing it to be easily molded around the ankle of a patient. A thicker material can be used, if desired, according to the amount of support needed. A cushioning material 24 is provided on an inner surface of the ankle brace 10 to cushion and protect the skin of the patient. Cushioning material 24 is in the form of a resilient foam adhered to the underside of the brace. A resilient sock or sleeve may be worn on the foot 26 by a patient prior to forming the thermoplastic sheet 11 around the ankle.

Ankle brace 10 is held in place around the ankle above the foot 26, preferably by a non-stretchable strap 28 of loop textured material having a buckle 29, that wraps around upper portion 20 of thermoplastic sheet 11, and is fastened in place with hook textured material pad 40. Calf strap 28 holds ankle brace 10 comfortably around the calf of a patient's leg 22, and is secured by loop textured material fastener 30.

Medial and lateral extensions 12 and 14 of the lower portion of thermoplastic sheet 11 are securely strapped by wrapping a stretchable strap 32 around the ankle in a figure-eight fashion. Ankle strap 32 is wrapped in a figure-eight fashion around the ankle from the medial extension under and supporting the longitudinal arch of the foot, to the front edge of the lateral extension, then around to the front of the ankle continuing around to the back of the ankle to the lateral extension and then fastening in the front by a loop textured fastener over the dorsum of the foot and is held in place by a loop textured fastener 36. These straps decrease distal tibia-fibular and subtalar motion.

Ankle strap 32 securely holds medial and lateral extensions 12 and 14 on medial and lateral malleoli 16 and 18, and act to restrain the foot and minimize medial and lateral instability. Medial extension 12 is designed to extend below the medial malleolus 16 to approximately halfway to the sole of foot 26 and it is very effective to prevent excessive inversion or subtalar motion which is the area most common in ankle injuries. That is the turning of the foot inward putting excessive stress on the lateral ligaments.

Medial and lateral extension 12 and 14, form splints to prevent excessive inversion/eversion of the ankle and reduce trauma to the ankle. Calf strap 28 has D-ring 29 that allows the strap to be pulled tightly and secured with VELCRO fastener 30.

Ankle brace 10 is shown in FIGS. 5 and 6 in place around the ankle of a patient with hook textured material 40 fastened to the surface of the thermoplastic sheet 11. Strategically placed hook textured material pads 42, 44 and 46 on the sides of thermoplastic sheet 11, and at the bottom of medial and lateral extensions 12 and 14. Hook textured material pad 40 wraps around thermoplastic sheet 11 and acts to hold calf strap 28 in position above the ankle to permit strap 28 to securely fasten ankle brace 10 in place.

Hook textured material pads 42, 44 and 46 are positioned to allow elastic strap 32 of loop textured material to be wrapped in a figure-eight fashion behind heel 34, beneath the sole of foot 26 and back over the dorsum to be fastened in place by another fastener which is also a hook textured material. The position and size of pads 42, 44 and 46 is arbitrary. They need to be sufficient to allow various configurations and tightness of the elastic strap to be used to hold extensions 12 and 14 securely in place over the medial and lateral malleoli to control subtalar and tibia-talar motions.

The construction and application of ankle brace 10 is illustrated in FIGS. 7 and 9. Ankle brace 10 is cut from a sheet of thermoplastic material 11 in a pattern similar to that shown in FIG. 7. In its flat position, thermoplastic sheet 11 has a substantially rectangular section and preformed medial and lateral extensions 12 and 14. Preferably, medial extension 12 has a curved heel recess 13 to fit around the portion of the heel just below the medial malleolus.

With thermoplastic material 11 cut to form medial and lateral extensions 12, 14, recess 50 is formed to allow extensions 12 and 14 to permit plantar flexion and dorsiflexion while stabilizing against ankle inversion and eversion. To improve the strength of pre-cut thermoplastic sheet 11, distal end of recess 50 is formed with concave section 52 that improves the strength of and comfort of the ankle brace when the edge is rolled and resists cracking when being fitted around a patient's ankle. Hook-textured material pads 40, 42, 44 and 46 are applied after fitting the brace around a patient's ankle, but could be attached earlier.

Ankle brace 10 is applied to the injured ankle of the patient, as illustrated in FIGS. 8 and 9. Before application to a patient, thermoplastic pattern 11 is preferably heated in hot water 54 at a temperature in the range of 140° F. to 170° F. in tank 55, or by some other suitable means to soften the thermoplastic material. Thermoplastic pattern 11, with medial extension 12 and lateral extension 14, is then wrapped around and carefully pressed against the ankle of a patient to form a secure, conformable splint to support an injured ankle. A patient is positioned and bone prominences are padded as necessary and appropriate.

Cushioning material may be applied to a thermoplastic sheet 11, before it is applied to the foot 26 of a patient or a resilient foam or neoprene sock or sleeve slipped over foot 26 of the patient is an option. When in place, around an injured ankle, the moldable custom form-fitting brace wraps around up to 70 to 80 percent of the wearers tibia and fibula providing substantial support where needed.

An advantage of the conformable ankle brace 10 is that it can be reformed as often as necessary for changes in the condition of an injured ankle of a patient. As swelling decreases ankle brace 10 can be reformed to provide secure, comfortable support to an injured ankle. This is achieved by removing straps 28 and 32 and reheating the brace to soften the material. The brace may then be re-formed around the ankle of a patient.

Preferably, the thermoplastic material is an NCM Clinic D thermoplastic sheet approximately ⅛the of an inch thick that is easily trimmed with scissors.

An optional construction for the material of the conformable ankle brace 10 is illustrated in FIGS. 10 and 11. The embodiments of FIGS. 2 and 4 show a heat formable thermoplastic material having a cushioning foam or thermoplastic sheet. As was previously stated, the thickness can vary to provide the support needed as desired. However, a method of improving the strength of the heat formable plastic material is by the addition of a reinforcing material 60 between the thermal plastic sheet 11 and the resilient foam cushioning material 24. The reinforcing material can be a synthetic natural such as that known by the trademark "STERI-STRIP" or similar material but could be a thin fiberglass material. Reinforcing material 60, adhered to the surface of thermoplastic sheet 11, provides additional strength and cohesiveness while still allowing the thermoplastic sheet to be heat formable around the ankle of a patient. STERI-STRIP type material is preferred for strengthening backing 60 because of its flexibility while still adding considerable strength and cohesiveness to the construction.

In this embodiment, reinforcing material 60 may be adhered to the surface of thermoplastic sheet 11 by any suitable method such as using an adhesive. Optionally, the thermoplastic material could be heated enough to reach nearly a melting point so that reinforcing material 60 bonds to the surface of the thermoplastic sheet. Resilient foam backing 24 can then be adhered to the surface of reinforcing material 60, or simply placed in position beneath the laminated construction of the thermoplastic sheet and bonded reinforcing material 60.

A third embodiment, employing a laminated construction is illustrated in FIG. 11. In this embodiment, conformable ankle brace 10 is constructed of a pair of thermoplastic sheets 11 and 11', having a reinforcing material 62 between them. Reinforcing material 62 can be bonded to thermoplastic sheets 11 and 11' by any suitable methods such as adhesive or by heat treating as desired. Cushioning foam sheet 24 would then be bonded to or cushion the surface of thermoplastic sheet 11'.

A wide range of variations can be employed to construct the conformable ankle brace 10 of the invention. For example, the embodiment shown in FIG. 11 can have a relatively thick thermoplastic 11 on the outer surface and a thinner thermoplastic sheet 11' sandwiching reinforcing material 62 between then. Thus, the thickness of thermoplastic sheets 11 and 11' and fiberglass sheeting 62 can be varied as needed to provide the amount of support ad strengthening required. The reinforcing materials 62 can be varied as needed to provide the amount of support and strengthening required. The fiberglass reinforcing 60 and 62 shown in the embodiments of FIGS. 10 and 11 can improve the structural strength of the conformable ankle brace 10 to prevent cracking, while at the same time, allowing the material to be heated and formed around an ankle.

The ankle brace of the present invention has a number of advantages in addition to conforming to the shape of the patient's ankle by simply heating it and forming it in place. The upper section of thermoplastic sheet 11 can be longer to allow the upper portion 20 (FIG. 5) to extend and completely cover the tibia to act as shin guards for athletes if desired. Thus, the ankle brace not only acts as an ankle brace, but could also incorporate an integrally formed shin guard.

An optional embodiment of the invention is to replace straps 28 and 30 with tape securely wrapped around and holding the conformable custom-fitted ankle brace in place. Strapping is done with athletic tape eliminating the need for straps 28 and 30. The tape may be wrapped in a figure-eight fashion similar to strap 30, and then wrapped several times around the leg until the brace is completely covered. This configuration has several advantages over the conventional taping of ankle braces used by athletes. Since ankle brace 10 is custom-fitted and provides substantial support, much less tape is needed. All that is needed is enough tape to hold the brace firmly in place. The taping is also less critical since tape along requires very careful application of several layers. The conformable custom-fitted ankle brace disclosed when taped in place, provides substantial, comfortable support without the discomfort and disadvantages of present methods and devices.

Thus, there has been described a unique conformable ankle brace that has a wide range of applications that is simple in construction and easy to use. The ankle brace is made of a thermoplastic material to allow it to comfortably conform to the shape of a patient's injured ankle. The construction also allows holding straps or athletic tape to be tightly wrapped in the most comfortable position to provide maximum support with minimum discomfort. Optionally, the strapping may be done with athletic tape eliminating the need for hook and look textured material fasteners. The heat formable ankle brace provides a vise-like clamping action for listal-tibia fibular joint.

This invention is not to be limited by the embodiment shown in the drawings and described in the description which is given byway of example and not of limitation, but only in accordance with the scope of the appended claims.

What is claimed is:

1. A conformable ankle brace comprising:
   a heat formable thermoplastic sheet;
   a lateral extension on said thermoplastic sheet;
   a medial extension on said thermoplastic sheet;
   a cushioning material covering an inner side of said thermal sheet;
   strap holding means secured to the other side of said thermal sheet;
   said medial and lateral extension constructed to extend below and completely cover the medial and lateral malleoli of a foot and forming a recess constructed to fit around the upper portion of a foot;
   said recess in said thermoplastic sheet having a concave distal end formed to strengthen said thermal sheet;
   a plurality of straps removably secured to said strap holding means for securing said ankle brace;
   whereby said heat formable thermoplastic sheet may be softened with heat and then form-fitted to an ankle with said lateral and medial extensions extending below and covering the lateral and medial malleoli on either side of the foot.

2. The ankle brace according to claim 1 wherein said strap holding means comprises hook textured material secured to the outer side of said thermoplastic sheet to hold said straps in place.

3. The ankle brace according to claim 2 in which said thermoplastic sheet has a rectangular portion constructed to conform and fit around the shin bone.

4. The ankle brace according to claim 1 in which said thermoplastic sheet is a material and thickness selected to be easily trimmed when warmed; whereby, said conformable ankle brace can be easily trimmed to fit when being formed around an injured ankle.

5. The ankle brace according to claim 4 including reinforcing means for reinforcing said thermoplastic sheet to prevent cracking.

6. The ankle brace according to claim 5 in which said reinforcing means comprises; a reinforcing backing bonded to said thermoplastic sheet.

7. The ankle brace according to claim 6 in which said reinforcing backing is a backing bonded to said thermoplastic sheet and a second thermoplastic sheet bonded to said backing forming a laminated construction.

8. The ankle brace according to claim 7 in which said second thermoplastic sheet is thinner than the thermoplastic sheet.

9. The ankle brace according to claim 1 in which said plurality of straps comprise: a non-stretching calf strap having a loop textured material for holding said strap on said heat formable thermoplastic sheet; an elongate stretchable strap having loop textured material to secure to said preformed thermal sheet, said elongate stretchable strap having a length selected to form a figure-eight wrap around the heed, under the sole and over the dorsum of a foot.

10. The ankle brace according to claim 1 in which said medial extension has a length that extends approximately to midway between the malleolus and the sole of the foot.

11. The ankle brace according to claim 1 in which said cushioning material is a resilient foam liner secured to said thermoplastic sheet.

12. A method of bracing an ankle comprising:
   forming a sheet of thermoplastic material with medial and lateral extensions constructed to extend below and completely cover the medial and lateral malleoli of a foot, said thermoplastic material selected to have a thickness that allows it to be easily trimmed when warmed;
   forming said thermoplastic sheet with a concave recess between said medial and lateral extensions to strengthen said thermoplastic sheet to reduce cracking;
   heating said thermoplastic sheet until it is pliable;
   forming said heating thermoplastic sheet in place around said ankle with said medial extensions extending below and covering the medial malleolus and said lateral extension extending below and covering the lateral malleolus;

providing a cushioning and lining material beneath said thermoplastic sheet;

securing strap holding means to hook textured material on the exterior side of said thermoplastic sheet to hold said formed thermoplastic sheet in place around said ankle and lower leg;

wrapping a non-stretchable strap around the calf to securely hold said thermoplastic sheet against a shin of a patient above said ankle;

wrapping a stretchable strap under the sole and over the dorsum of a foot and around the ankle to secure said lateral extension and medial extension in place over the lateral and medial malleoli respectively;

whereby an injured ankle can be supported by a brace that conforms to the shape of a patient's ankle.

13. The method according to claim 12 in which said cushioning comprises securing a resilient foam material to the underside of said thermoplastic sheet.

14. The method according to claim 12 including reinforcing means for reinforcing said thermoplastic sheet to prevent cracking.

15. The method according to claim 13 in which said reinforcing means comprises; a reinforcing material backing said thermoplastic sheet.

16. The method according to claim 15 in which said reinforcing backing is a backing bonded to said thermoplastic sheet and a second thermoplastic sheet bonded to said backing forming a laminated construction.

17. The method according to claim 16 in which said second thermoplastic sheet is thinner than the thermoplastic sheet.

18. The method according to claim 12 in which securing strap holding means comprises securing hook textured material pads to the exterior of said thermoplastic sheet.

19. A moldable custom-fitted ankle brace comprising:

a heat formable thermoplastic sheet of material having a thickness selected to be easily trimmed when warmed;

a medial extension formed in said thermoplastic sheet constructed to extend to and fit over the medial malleolus to near thesole of a foot;

a lateral extension formed in said thermoplastic sheet constructed to fit over the lateral malleolus when said brace is formed around said ankle;

strap means for holding said custom-fitted ankle brace in place; and a concave recess formed between said medial and lateral extensions to strengthen and reduce cracking of said thermoplastic sheet;

said medial and lateral extensions being held in place around an ankle by said strap means so that pronation and subtalar inversion are decreased;

whereby said thermoplastic sheet may be softened with heat, form-fitted to an injured ankle and secured by said straps to decrease movement of the distal tibia-joint and stabilize the heel.

20. The ankle brace according to claim 19 wherein said straps are comprised of an elastic material and include hook and loop textured fasteners to hold said ankle brace securely in place.

21. The ankle brace according to claim 20 in which said thermoplastic sheet has a rectangular portion constructed to conform and fit around the tibia.

22. The ankle brace according to claim 21 in which said thermoplastic sheet is selected of a material and thickness that can be easily cut whereby said conformable ankle brace can be easily trimmed to fit when being formed around an injured ankle.

23. The ankle brace according to claim 22 including reinforcing means for reinforcing said thermoplastic sheet to prevent cracking.

24. The ankle brace according to claim 23 in which said reinforcing means comprises; a reinforcing backing bonded to said thermoplastic sheet.

25. The ankle brace according to claim 24 in which said reinforcing backing is a fiberglass backing bonded to said thermoplastic sheet and a second thermoplastic sheet bonded to said fiberglass backing forming a laminated construction.

26. The ankle brace according to claim 25 in which said second thermoplastic sheet is thinner than the thermoplastic sheet.

27. A method of forming a form-fitted ankle brace comprising:

selecting a heat formable material that can be easily trimmed when warmed;

forming a lateral extension in said heat formable material constructed to fit over the lateral malleolus when said brace is formed around an injured ankle;

forming a longer medial extension in said heat formable material constructed to angled to fit over the medial malleolus when said brace is formed around an inured ankle;

securing said heat formable material in place around an injured ankle with strapping material;

forming a concave recess between said lateral and medial extensions to strengthen and reduce cracking of said ankle brace;

holding said medial and lateral extensions in place around an injured ankle by said straps so that pronation and subtalar inversion and eversion are decreased;

whereby said heat formable material may be softened with heat and form-fitted to an injured ankle and secured by said strapping to decrease movement of the distal tibula-joint and stabilize the heel.

28. The method according to claim 27 including adhering a cushioning material to the surface of said heat formable material.

29. The method according to claim 27 in which said strapping material is an elastic strap having hook and loop textured fasteners.

30. The method according to claim 27 in which said strapping material is an athletic adhesive tape.

31. The method according to claim 27 in which said heat formable material is a material and thickness selected to be easily trimmed when warmed whereby said conformable ankle brace can be easily formed around an injured ankle.

32. The method according to claim 31 in which said heat formable material is a thermoplastic sheet material.

33. The method according to claim 32 including reinforcing means for reinforcing said thermoplastic sheet to prevent cracking.

34. The method according to claim 33 in which said reinforcing means comprises; a reinforcing backing bonded to said thermoplastic sheet.

35. The method according to claim 34 in which said reinforcing backing is a backing bonded to said thermoplastic sheet and a second thermoplastic sheet bonded to said fiberglass backing forming a laminated construction.

36. The method according to claim 35 in which said second thermoplastic sheet is thinner than the thermoplastic sheet.

* * * * *